(12) United States Patent
Peterson

(10) Patent No.: US 11,951,300 B2
(45) Date of Patent: *Apr. 9, 2024

(54) AUTOMATIC LEAD IDENTIFICATION USING ELECTRIC FIELD FINGERPRINTING

(71) Applicant: Boston Scientific Neuromodulation Corporation, Valencia, CA (US)

(72) Inventor: David K. L. Peterson, Novato, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/752,581

(22) Filed: May 24, 2022

(65) Prior Publication Data

US 2022/0280772 A1 Sep. 8, 2022

Related U.S. Application Data

(63) Continuation of application No. 16/719,793, filed on Dec. 18, 2019, now Pat. No. 11,383,077, which is a
(Continued)

(51) Int. Cl.
*A61N 1/08* (2006.01)
*A61N 1/02* (2006.01)
(Continued)

(52) U.S. Cl.
CPC .......... *A61N 1/025* (2013.01); *A61N 1/36185* (2013.01); *A61N 1/0553* (2013.01); *A61N 1/37241* (2013.01); *A61N 1/37247* (2013.01)

(58) Field of Classification Search
CPC .. A61N 1/36185; A61N 1/0553; A61N 1/025; A61N 1/04; A61N 2001/083
See application file for complete search history.

(56) References Cited

U.S. PATENT DOCUMENTS 5,441,520 A 8/1995 Olsen
6,516,227 B1 2/2003 Meadows et al.
(Continued)

FOREIGN PATENT DOCUMENTS

WO WO-2010051495 A1 5/2010
WO WO-2011057213 5/2011

OTHER PUBLICATIONS

U.S. Appl. No. 12/941,657 U.S. Pat. No. 9,731,106, filed Nov. 8, 2010, Automatic Lead Identification Using Electric Field Fingerprinting.
(Continued)

*Primary Examiner* — Jon Eric C Morales
(74) *Attorney, Agent, or Firm* — Schwegman Lundberg & Woessner, P.A.

(57) ABSTRACT

A method, programmer for a neurostimulator, and neurostimulation kit are provided. The kit comprises a neurostimulator, and a plurality of elongated lead bodies configured for being coupled to the neurostimulator, each having a plurality of proximal contacts and a plurality of distal electrodes respectively electrically coupled to the proximal contacts, wherein an in-line connectivity between the electrodes and proximal contacts carried by the different lead bodies differs from each other. Electrical energy is conveyed between the electrodes of the selected lead body and the tissue, an electrical fingerprint is measured at the proximal contacts of the selected lead body in response to the conveyed electrical energy, and the selected lead body is identified based on the measured electrical fingerprint. These steps can be performed by the programmer.

20 Claims, 9 Drawing Sheets

Related U.S. Application Data continuation of application No. 16/050,546, filed on Jul. 31, 2018, now Pat. No. 10,549,085, which is a continuation of application No. 15/674,769, filed on Aug. 11, 2017, now Pat. No. 10,052,475, which is a continuation of application No. 12/941,657, filed on Nov. 8, 2010, now Pat. No. 9,731,106.

(60) Provisional application No. 61/259,509, filed on Nov. 9, 2009.

(51) Int. Cl.
*A61N 1/05* (2006.01)
*A61N 1/36* (2006.01)
*A61N 1/372* (2006.01)

(56) References Cited

U.S. PATENT DOCUMENTS

| | | | |
|---|---|---|---|
| 6,895,280 | B2 | 5/2005 | Meadows et al. |
| 6,993,384 | B2 | 1/2006 | Bradley et al. |
| 7,317,948 | B1 | 1/2008 | King et al. |
| 7,650,184 | B2 | 1/2010 | Walter |
| 9,731,106 | B2 | 8/2017 | Peterson |
| 10,052,475 | B2 | 8/2018 | Peterson |
| 10,549,085 | B2 | 2/2020 | Peterson |
| 11,383,077 | B2 * | 7/2022 | Peterson .............. A61N 1/025 |
| 2004/0122295 | A1 | 6/2004 | Hatlestad et al. |
| 2004/0162591 | A1 | 8/2004 | Jorgenson et al. |
| 2007/0150034 | A1 | 6/2007 | Rooney et al. |
| 2007/0150036 | A1 | 6/2007 | Anderson |
| 2007/0168004 | A1 | 7/2007 | Walter |
| 2008/0065181 | A1 | 3/2008 | Stevenson et al. |
| 2008/0183256 | A1 | 7/2008 | Keacher |
| 2010/0121409 | A1 | 5/2010 | Kothandaraman et al. |
| 2010/0137929 | A1 | 6/2010 | Libbey et al. |
| 2010/0137943 | A1 | 6/2010 | Zhu |
| 2011/0112609 | A1 | 5/2011 | Peterson |
| 2012/0239115 | A1 | 9/2012 | Lee |
| 2013/0116751 | A1 | 5/2013 | Moffitt et al. |
| 2017/0340875 | A1 | 11/2017 | Peterson |
| 2018/0333570 | A1 | 11/2018 | Peterson |
| 2020/0121913 | A1 | 4/2020 | Peterson |

OTHER PUBLICATIONS

U.S. Appl. No. 15/674,769 U.S. Pat. No. 10,052,475, filed Aug. 11, 2017, Automatic Lead Identification Using Electric Field Fingerprinting.
U.S. Appl. No. 16/050,546 U.S. Pat. No. 10,549,085, filed Jul. 31, 2018, Automatic Lead Identification Using Electric Field Fingerprinting.
U.S. Appl. No. 16/719,793, filed Dec. 18, 2019, Automatic Lead Identification Using Electric Field Fingerprinting.
"U.S. Appl. No. 12/941,657, Advisory Action dated Apr. 8, 2013", 3 pgs.
"U.S. Appl. No. 12/941,657, Appeal Brief filed Jun. 22, 2013", 12 pgs.
"U.S. Appl. No. 12/941,657, Appeal Brief filed Oct. 23, 2013", 11 pgs.
"U.S. Appl. No. 12/941,657, Appeal Decision mailed May 2, 2016", 8 pgs.
"U.S. Appl. No. 12/941,657, Examiner Interview Summary dated Mar. 15, 2017", 3 pgs.
"U.S. Appl. No. 12/941,657, Examiner's Answer mailed Jan. 10, 2014", 8 pgs.
"U.S. Appl. No. 12/941,657, Final Office Action dated Jan. 19, 2017", 9 pgs.
"U.S. Appl. No. 12/941,657, Final Office Action dated Jan. 28, 2013", 8 pgs.
"U.S. Appl. No. 12/941,657, Non Final Office Action dated Jul. 12, 2016", 9 pgs.
"U.S. Appl. No. 12/941,657, Non Final Office Action dated Aug. 27, 2013", 9 pgs.
"U.S. Appl. No. 12/941,657, Non Final Office Action dated Oct. 5, 2012", 8 pgs.
"U.S. Appl. No. 12/941,657, Notice of Allowance dated Apr. 18, 2017", 7 pgs.
"U.S. Appl. No. 12/941,657, Reply Brief filed Feb. 4, 2014", 3 pgs.
"U.S. Appl. No. 12/941,657, Response filed Mar. 14, 2017 to Final Office Action dated Jan. 19, 2017", 11 pgs.
"U.S. Appl. No. 12/941,657, Response filed Mar. 28, 2013 to Final Office Action dated Jan. 28, 2013", 4 pgs.
"U.S. Appl. No. 12/941,657, Response filed Oct. 10, 2016 to Non Final Office Action dated Jul. 12, 2016", 8 pgs.
"U.S. Appl. No. 12/941,657, Response filed Dec. 19, 2012 to Non Final Office Action dated Oct. 5, 2012", 4 pgs.
"U.S. Appl. No. 15/674,769, Non Final Office Action dated Sep. 5, 2017", 6 pgs.
"U.S. Appl. No. 15/674,769, Non Final Office Action dated Sep. 14, 2017", 7 pgs.
"U.S. Appl. No. 15/674,769, Notice of Allowance dated Apr. 20, 2018", 6 pgs.
"U.S. Appl. No. 15/674,769, Preliminary Amendment filed Aug. 30, 2017", 8 pgs.
"U.S. Appl. No. 15/674,769, Response filed Dec. 12, 2017 to Non Final Office Action dated Sep. 14, 2017", 7 pgs.
"U.S. Appl. No. 16/050,546, 312 Amendement filed Dec. 10, 2019", 9 pgs.
"U.S. Appl. No. 16/050,546, Advisory Action dated Mar. 13, 2019", 3 pgs.
"U.S. Appl. No. 16/050,546, Final Office Action dated Dec. 18, 2018", 15 pgs.
"U.S. Appl. No. 16/050,546, Non Final Office Action dated Apr. 29, 2019", 7 pgs.
"U.S. Appl. No. 16/050,546, Non Final Office Action dated Sep. 6, 2018".
"U.S. Appl. No. 16/050,546, Notice of Allowance dated Sep. 11, 2019", 8 pgs.
"U.S. Appl. No. 16/050,546, Preliminary Amendment filed Aug. 2, 2018", 9 pgs.
"U.S. Appl. No. 16/050,546, Response filed Feb. 11, 2019 to Final Office Action dated Dec. 18, 2018", 14 pgs.
"U.S. Appl. No. 16/050,546, Response filed Jul. 18, 2019 to Non Final Office Action dated Apr. 29, 2019", 9 pgs.
"U.S. Appl. No. 16/050,546, Response filed Nov. 27, 2018 to Non Final Office Action dated Sep. 6, 2018", 13 pgs.
"U.S. Appl. No. 16/719,793, Non Final Office Action dated Oct. 8, 2021", 22 pgs.
"U.S. Appl. No. 16/719,793, Notice of Allowance dated Mar. 9, 2022", 7 pgs.
"U.S. Appl. No. 16/719,793, Preliminary Amendment filed Dec. 23, 2019", 7 pgs.
"U.S. Appl. No. 16/719,793, Response filed Dec. 14, 21 to Non Final Office Action dated Oct. 8, 2021", 11 pgs.
"Australian Application Serial No. 2010314896, Office Action dated Feb. 2, 2015", 4 pgs.
"Australian Application Serial No. 2010314896, Subsequent Examiners Report dated Oct. 15, 2015", 3 pgs.
"Canadian Application Serial No. 2,780,014, Office Action dated Oct. 7, 2016", 4 pgs.
"European Application Serial No. 10778799.6, Communication Pursuant to Article 94(3) EPC dated Dec. 5, 2017", 7 pgs.
"European Application Serial No. 10778799.6, Office Action dated Jul. 18, 2012", 2 pgs.
"European Application Serial No. 10778799.6, Response filed Dec. 21, 2012 to Office Action dated Jul. 18, 2012", 9 pgs.
"International Application Serial No. PCT/US2010/055863, International Search Report dated Feb. 4, 2011", 4 pgs.
"International Application Serial No. PCT/US2010/055863, Written Opinion dated Feb. 4, 2011", 4 pgs.
"International Application Serial No. PCT/US2010/055868, International Preliminary Report on Patentability dated May 24, 2012", 10 pgs.

(56) References Cited

OTHER PUBLICATIONS

"International Application Serial No. PCT/US2010/055868, International Search Report dated Sep. 19, 2013", 6 pgs.
"International Application Serial No. PCT/US2010/055868, Written Opinion dated Sep. 19, 2013", 8 pgs.
Barker, John Michael, et al., "Temporary Neurostimulation Lead Identification Device", File History of U.S. Appl. No. 61/030,506, (filed Feb. 21, 2008).

* cited by examiner

AUTOMATIC LEAD IDENTIFICATION USING ELECTRIC FIELD FINGERPRINTING

RELATED APPLICATION

The present application is a continuation of application Ser. No. 16/719,793, filed Dec. 18, 2019, which is a continuation of U.S. application Ser. No. 16/050,546, filed Jul. 31, 2018, now issued as U.S. Pat. No. 10,549,085, which is a continuation of U.S. application Ser. No. 15/674,769, filed Aug. 11, 2017, now issued as U.S. Pat. No. 10,052,475, which is a continuation of U.S. application Ser. No. 12/941,657, filed Nov. 8, 2010, now issued as U.S. Pat. No. 9,731,106, which claims the benefit under 35 U.S.C. § 119 to U.S. provisional patent application Ser. No. 61/259,509, filed Nov. 9, 2009. The foregoing applications are hereby incorporated by reference into the present application in their entirety.

FIELD OF THE INVENTION

The present invention relates to tissue stimulation systems, and more particularly, to apparatus and methods for identifying neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more stimulation leads implanted at the desired stimulation site and an implantable neurostimulator, such as an implantable pulse generator (IPG), implanted remotely from the stimulation site, but coupled either directly to the stimulation leads or indirectly to the stimulation leads via one or more lead extensions in cases where the length of the stimulation leads is insufficient to reach the IPG. Thus, electrical pulses can be delivered from the neurostimulator to the stimulation leads to stimulate the tissue and provide the desired efficacious therapy to the patient.

In the context of an SCS procedure, one or more stimulation leads are introduced through the patient's back into the epidural space under fluoroscopy, such that the electrodes carried by the leads are arranged in a desired pattern and spacing to create an electrode array. The specific procedure used to implant the stimulation leads will ultimately depend on the type of stimulation leads used. Currently, there are two types of commercially available stimulation leads: a percutaneous lead and a surgical lead.

A percutaneous lead comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline.

A surgical lead has a paddle on which multiple electrodes are arranged in independent columns, and is introduced into contact with the affected spinal tissue using a surgical procedure, and specifically, a laminectomy, which involves removal of the laminar vertebral tissue to allow both access to the dura layer and positioning of the lead.

After proper placement of the stimulation leads at the target area of the spinal cord, the leads are anchored in place at an exit site to prevent movement of the stimulation leads. To facilitate the location of the neurostimulator away from the exit point of the stimulation leads, lead extensions are sometimes used. Whether lead extensions are used or not, the proximal ends of the stimulation leads exiting the spinal column are passed through a tunnel subcutaneously formed along the torso of the patient to a subcutaneous pocket (typically made in the patient's abdominal or buttock area) where a neurostimulator is implanted. The subcutaneous tunnel can be formed using a tunneling tool over which a tunneling straw may be threaded. The tunneling tool can be removed, the stimulation leads threaded through the tunneling straw, and then the tunneling straw removed from the tunnel while maintaining the stimulation leads in place within the tunnel.

The stimulation leads are then connected directly to the neurostimulator by inserting the proximal ends of the stimulation leads within one or more connector ports of the IPG or connected to lead extensions, which are then inserted into the connector ports of the IPG. The IPG can then be operated to generate electrical pulses that are delivered, through the electrodes, to the targeted tissue, and in particular, the dorsal column and dorsal root fibers within the spinal cord.

The stimulation creates the sensation known as paresthesia, which can be characterized as an alternative sensation that replaces the pain signals sensed by the patient. Intraoperatively during the surgical procedure), the neurostimulator may be operated to test the effect of stimulation and adjust the parameters of the stimulation for optimal pain relief. The patient may provide verbal feedback regarding the presence of paresthesia over the pain area, and based on this feedback, the lead positions may be adjusted and re-anchored if necessary. A computerized programming system, such as Bionic Navigator®, available from Boston Scientific Corporation, can be used to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

Oftentimes, multiple lead bodies may extend from the spinal region of the patient. For example, multiple percutaneous leads may be implanted within the patient adjacent the spinal cord, or in the case of paddle leads, multiple lead tails may extend from the paddle, with each lead tail being coupled to specific electrodes on the paddle. Because the programming of the IPG will depend upon the physical locations of the electrodes relative to the patient's spinal cord, the proximal ends of the lead bodies are labeled before passing them through the tunneling straw, so that the surgeon can keep track of which set of electrodes is connected to which connector port on the implanted IPG (which may include up to four ports in the near future), or if multiple IPGs are to be implanted, which set of electrodes is connected to which IPG.

One technique used by surgeons to identify the lead bodies is to tie sutures around the proximal ends of the lead bodies prior to introducing them through the tunneling straw; for example, one suture around a first lead body, two sutures around a second lead body, three sutures around a third lead body, etc. Once the proximal ends of the lead bodies exit the tunneling straw, the surgeon can then identify each lead body (and thus the corresponding electrodes) by the number of sutures tied to the respective lead body, thereby allowing the lead body to be connected to the correct port on the IPG.

While this technique can be successfully employed to identify lead bodies, it considerably extends the length of the surgery time, which is undesirable. In some cases, the identification features, such as different colors or markings, can be incorporated into the proximal ends of the lead bodies, such that the lead bodies can be identified as they exit the tunneling straw. Even with the use of visual identifiers, however, the proximal ends of the lead bodies can still be inserted into the incorrect connector ports. If the lead bodies are inserted into the incorrect connector ports, intra-operative testing of the lead placement may be compromised. Additional surgical time may be wasted to identify and correct the connection problem. If the errors remain unidentified, the patient may leave the operating room with the lead bodies incorrectly connected. During post-operative fitting, additional time may then be lost identifying and compensating for lead bodies that are not in the proper connector ports. This ultimately can result in sub-optimal therapy.

Another related problem arises when different types of stimulation leads are used. During an intra-operative or post-operative procedure, the clinician is required to select the model of the stimulation lead or leads in order for the computerized programming system to operate in an optimal fashion. As the number of lead models increases, it becomes increasingly likely that the incorrect lead model will be selected.

There, thus, remains a need for a quick, effective, and low-cost method for identifying a lead body of a neurostimulation lead.

SUMMARY OF THE INVENTION

In accordance with a first aspect of the present inventions, a method of identifying a selected one of a plurality of different lead bodies is provided. The plurality of lead bodies may comprises, e.g., at least two lead bodies of a surgical paddle lead and/or a lead body of a surgical paddle lead and a lead body of a percutaneous lead. Each of the lead bodies includes a plurality of proximal contacts and a plurality of distal electrodes respectively electrically coupled to the proximal contacts. The selected lead body is in contact with tissue of a patient.

The method comprises conveying electrical energy between the electrodes of the selected lead body and the tissue. The method further comprises measuring an electrical fingerprint at the proximal contacts of the selected lead body in response to the conveyed electrical energy. By way of non-limiting example, the measured electrical fingerprint may comprise a plurality of electrical field potentials respectively measured at the proximal contacts of the selected lead body. The method further comprises identifying the selected lead body based on the measured electrical fingerprint. In one method, the in-line connectivity between the electrodes and proximal contacts carried by the different lead bodies differs from each other. In this manner, the measured electrical fingerprints will differ from each other.

By way of non-limiting example, the method may further comprise comparing the measured electrical fingerprint to each of a plurality of reference electrical fingerprints corresponding to the different lead bodies, determining a match between the measured electrical fingerprint and one of the reference electrical fingerprints, and identifying the selected lead body as the lead body corresponding to the matching one of the reference electrical fingerprints. The data points in the measured electrical fingerprint may be computationally compared to data points in each of the reference electrical fingerprints. For example, the computational comparison for each of the reference electrical fingerprints may comprise generating a correlation coefficient (e.g., a Pearson correlation coefficient), wherein a match between the measured electrical fingerprint and the one reference electrical fingerprint is determined based on the values of the generated correlation coefficients.

In accordance with a second aspect of the present inventions, a programmer for a neurostimulator is provided. The programmer comprises a user interface configured for receiving user commands, and input circuitry configured for receiving an electrical fingerprint measured by a neurostimulator connected to a lead body. The programmer further comprises a processor configured for automatically identifying the lead body from a plurality of different lead bodies based on the measured electrical fingerprint, and generating stimulation parameters for the identified lead body in response to the user commands. The plurality of lead bodies may comprises, e.g., at least two lead bodies of a surgical paddle lead and/or a lead body of a surgical paddle lead and a lead body of a percutaneous lead. By way of non-limiting example, the measured electrical fingerprint may comprise a plurality of electrical field potentials respectively measured at the proximal contacts of the selected lead body. The programmer further comprises output circuitry (e.g., telemetry circuitry) for transmitting the stimulation parameters to the neurostimulator.

In one embodiment, the programmer further comprises memory storing a plurality of reference electrical fingerprints corresponding to the different lead bodies. In this case, the processor is configured for comparing the measured electrical fingerprint to each of a plurality of reference electrical fingerprints, determining a match between the measured electrical fingerprint and one of the reference electrical fingerprints (e.g., in the manner discussed above), and identifying the selected lead body as the lead body corresponding to the matching one of the reference electrical fingerprints.

In accordance with a third aspect of the present inventions, an implantable neurostimulation kit is provided. The kit comprises a neurostimulator (e.g., an implantable pulse generator), and a plurality of elongated lead bodies configured for being coupled to the neurostimulator. Each of the lead bodies has a plurality of proximal contacts and a plurality of distal electrodes respectively electrically coupled to the proximal contacts. The in-line connectivity between the electrodes and proximal contacts carried by the different lead bodies differs from each other. By way of non-limiting example, the kit may further comprise at least one spinal cord stimulation lead having the plurality of lead bodies, a surgical paddle lead having the plurality of lead bodies and/or a surgical paddle having one of the plurality of lead bodies, and a percutaneous lead having another of the plurality of lead bodies.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
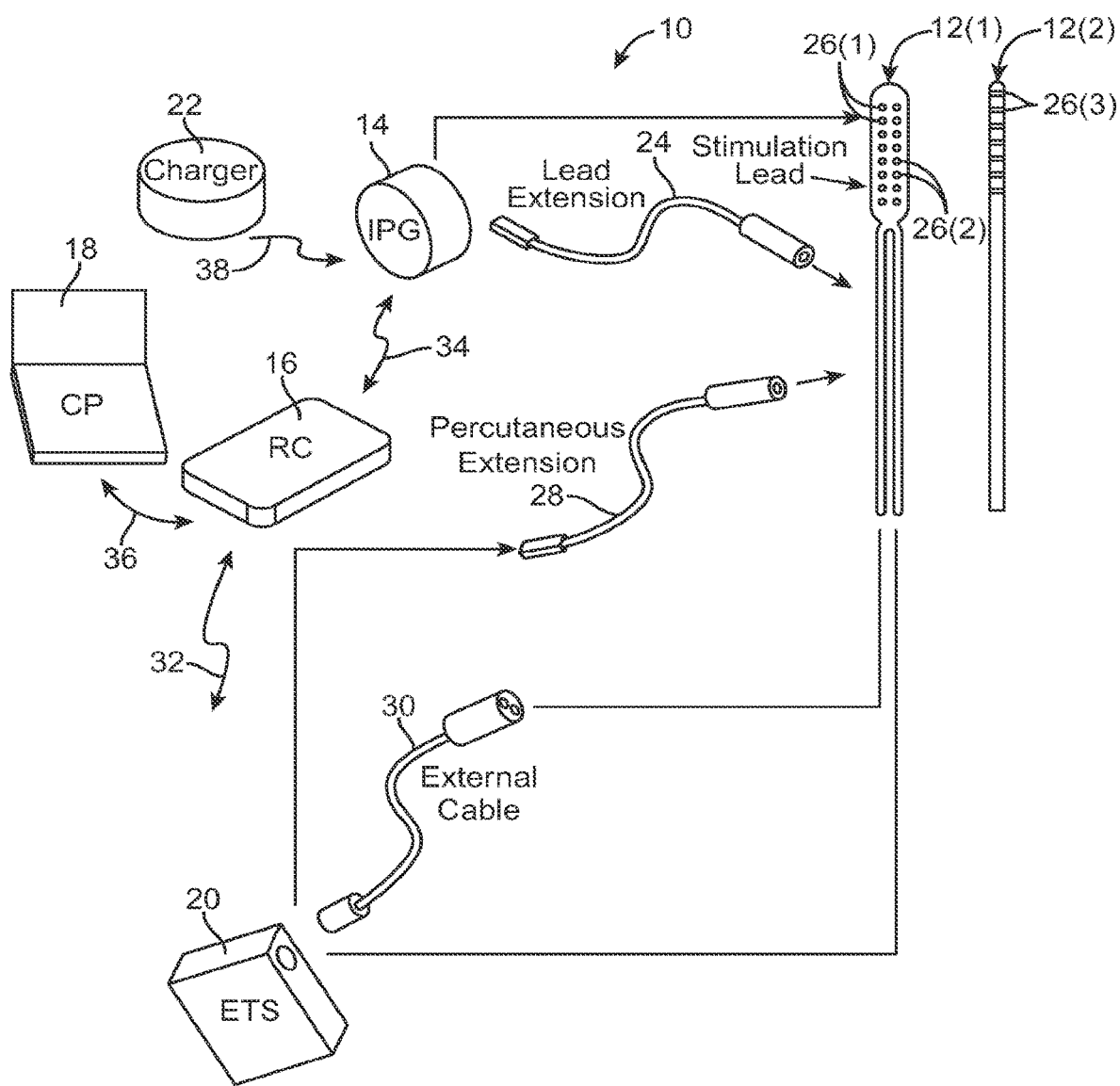
FIG. 1 is plan view of one embodiment of a spinal cord stimulation (SCS) system arranged in accordance with the present inventions.

Turning first to FIG. 1, an exemplary SCS system 10 generally comprises at least one implantable stimulation lead 12 (e.g., surgical paddle lead 12(1) and/or percutaneous lead 12(2)), an implantable pulse generator (IPG) 14, an external remote control RC 16, a Clinician's Programmer (CP) 18, an External Trial Stimulator (ETS) 20, and an external charger 22.

The IPG 14 is physically connected via one or more lead extensions 24 to the stimulation lead(s) 12, which carries a plurality of electrodes 26 (electrodes 26(1)-(3)) arranged in an array. In the illustrated embodiment, one of the stimulation leads that can be incorporated into the SCS system 10 is a surgical paddle lead 12(1) that carries electrodes 26(1)/(2), and another one of the stimulation leads that can be incorporated into the SCS system 10 is a percutaneous lead 12(2) that carries electrodes 26(3). Although only one surgical paddle lead 12(1) and only one percutaneous lead 12(2) are shown, multiple surgical paddle leads 12(1) and/or percutaneous leads 12(2) can be used with the SCS system 10. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The IPG 14 and stimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device."

The ETS 20 may also be physically connected via the percutaneous lead extensions 28 and external cable 30 to the stimulation lead 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RE communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36.

Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

As briefly discussed above, one of the stimulation leads may be a surgical paddle lead 12(1). To this end, and with reference to FIG. 2, the surgical paddle lead 12(1) comprises a paddle-shaped membrane 40, and two elongated lead bodies 42 (a first lead body 42(1) and a second lead body 42(2)) extending from the paddle-shaped membrane 40. Each of the lead bodies 42 has a proximal end 44 and a distal end 46. Each lead body 42 may, e.g., have a diameter within the range of 0.03 inches to 0.07 inches and a length within the range of 30 cm to 90 cm for spinal cord stimulation applications. Each lead body 42 may be composed of a suitable electrically insulative material, such as, a polymer (e.g., polyurethane or silicone), and may be extruded from as a unibody construction. The paddle-shaped membrane 40 is composed of an electrically insulative material, such as silicone.

The surgical paddle lead 12(1) further comprises proximal contacts 48 (proximal contacts 48(1) and proximal contacts 48(2)) mounted to the proximal ends 44 of the lead bodies 42 and the plurality of electrodes 26 mounted on one side of the paddle-shaped membrane 40 in a two-dimensional arrangement. In the illustrated embodiment, proximal contacts 48(1) are mounted to the proximal end 44 of the first lead body 42(1), proximal contacts 48(2) are mounted to the proximal end 44 of the second lead body 42(2), and the electrodes 26 are arranged as a first column of electrodes 26(1) and a second column of electrodes 26(2) on the membrane 40. As shown, the electrodes 26 are labeled as electrodes E1-E8 for each column, and the proximal contacts 48 are labeled as proximal contacts PC1-PC8 for each lead body 42. Although the stimulation lead 12(1) is shown as having sixteen electrodes 26 (and thus, eight corresponding proximal contacts on each lead body 36), the number of electrodes may be any number suitable for the application in which the surgical paddle lead 12(1) is intended to be used (e.g., two, four, eight, etc.).

Each of the electrodes 26 takes the form of a disk composed of an electrically conductive, noncorrosive, material, such as, e.g., platinum, titanium, stainless steel, or alloys thereof. Each of the proximal contacts 48 takes the form of a cylindrical ring element composed of an electrically conductive, biocompatible, noncorrosive, material, such as, e.g., platinum, titanium, stainless steel, or alloys thereof.

The surgical paddle lead 12(1) also includes a plurality of electrical conductors (not shown) extending through individual lumens (not shown) within each lead body 42 and connected between the respective proximal contacts 48 and electrodes 26 using suitable means, such as welding, thereby electrically coupling the proximal contacts 48(1) on the first lead body 42(1) to the first column of electrodes 26(1) and the proximal contacts 48(2) on the second lead body 42(2) to the second column of electrodes 26(2).

Further details regarding the construction and method of manufacture of paddle leads are disclosed in U.S. patent application Ser. No. 11/319,291, entitled "Stimulator Leads and Methods for Lead Fabrication." the disclosure of which is expressly incorporated herein by reference.

Significantly, as will be described in further detail below, the in-line connectivity between the proximal contacts 48(1) located on the first lead body 42(1) and the first column of electrodes 26(1), and the in-line connectivity between the proximal contacts 48(2) on the second lead body 42(2) and the second column of electrodes 26(2) differ from each other. That is, relative to the same physical ordering between the proximal contacts and electrodes, the order in which the proximal contacts 48(1) of the first lead body 42(1) is electrically connected to the first column of electrodes 26(1) differs from the order in which the proximal contacts 48(2) of the second lead body 42(2) is electrically connected to the second column of electrodes 26(2). As will be discussed in further detail below, the different in-line connectivities of the lead bodies 42 allows them to be electrically distinguished from each other, and thereby identified.

As briefly discussed above, another of the stimulation leads may be a percutaneous lead 12(3). To this end, and with reference to FIG. 3, the percutaneous lead 12(3) comprises an elongated lead body 42(3) having a proximal end 44 and a distal end 46. The lead body 42(3) may, e.g., have a diameter within the range of 0.03 inches to 0.07 inches and a length within the range of 30 cm to 90 cm for spinal cord stimulation applications. The lead body 42(3) may be composed of a suitable electrically insulative material, such as, a polymer (e.g., polyurethane or silicone), and may be extruded from as a unibody construction.

The percutaneous lead 12(2) further comprises a plurality of proximal contacts 48(3) mounted to the proximal end 44 of the lead body 48(3) and the plurality of in-line electrodes 26(3) mounted to the distal end 46 of the lead body 48(3). As shown, the electrodes 26(3) are labeled as electrodes E1-E8, and the proximal contacts 48(3) are labeled as proximal contacts PC1-PC8. Although the percutaneous lead 12(2) is shown as having eight electrodes 26(3) (and thus, eight corresponding proximal contacts 48(3)), the number of electrodes may be any number suitable for the application in which the percutaneous lead 12(2) is intended to be used (e.g., two, four, sixteen, etc.). Each of the electrodes 26 and proximal contacts 48 takes the form of a cylindrical ring element composed of an electrically conductive, biocompatible, non-corrosive, material, such as, e.g., platinum, titanium, stainless steel, or alloys thereof, which is circumferentially disposed about the lead bodies.

The percutaneus lead 12(2) also includes a plurality of electrical conductors (not shown) extending within the lead body 42(3) and connected between the respective proximal contacts 48(3) and electrodes 26(3) using suitable means, such as welding, thereby electrically coupling the proximal contacts 48(3) with the distally-located electrodes 26(3). The percutaneous lead 12(2) further includes a central lumen (not shown) that may be used to accept an insertion stylet (described in further detail below) to facilitate lead implantation.

Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Significantly, as will be described in further detail below, the in-line connectivity between the proximal contacts 48(3) and electrodes 26(3) of the percutaneous lead 12(2), and the in-line connectivities between the proximal contacts 48(1)/(2) and electrodes 26(1)/(2) of the surgical paddle lead 12(1) differ from each other. That is, relative to the same physical ordering between the proximal contacts and electrodes, the order in which the proximal contacts 48(3) of the lead body 42(3) is electrically connected to the electrodes 26(3) differs from the order in which the proximal contacts 48(1) of the first lead body 42(1) of the surgical paddle lead 12(1) is electrically connected to the first column of electrodes 26(1), and further differs from the order in which the proximal contacts 48(2) of the second lead body 42(2) of the surgical paddle lead 12(1). As will be discussed in further detail below, the different in-line connectivities of the lead bodies 42 allows them to be electrically distinguished from each other, and thereby identified.

Figure 2:
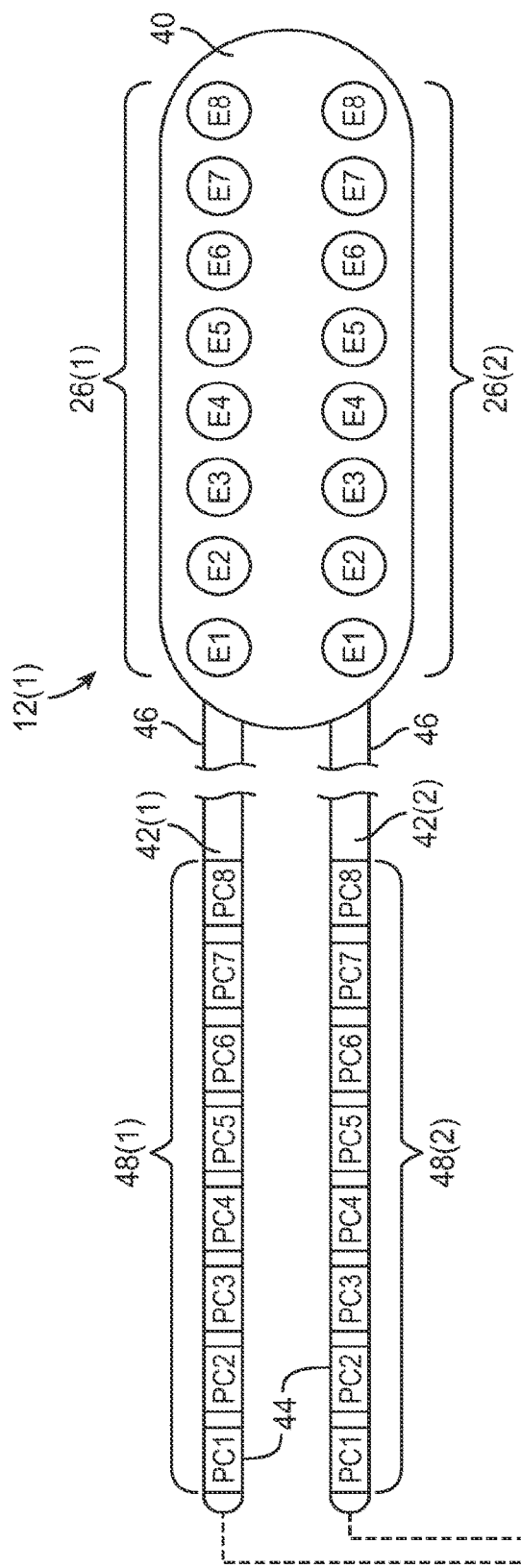
FIG. 2 is a plan view of an implantable pulse generator (IPG) and one embodiment of a surgical paddle stimulation lead used in the SCS system of FIG. 1.
Figure 2:
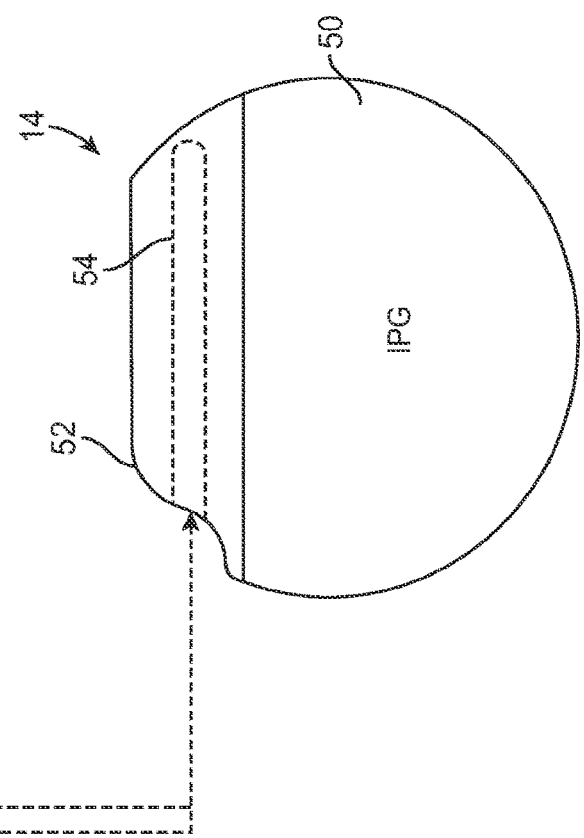
Figure 3:
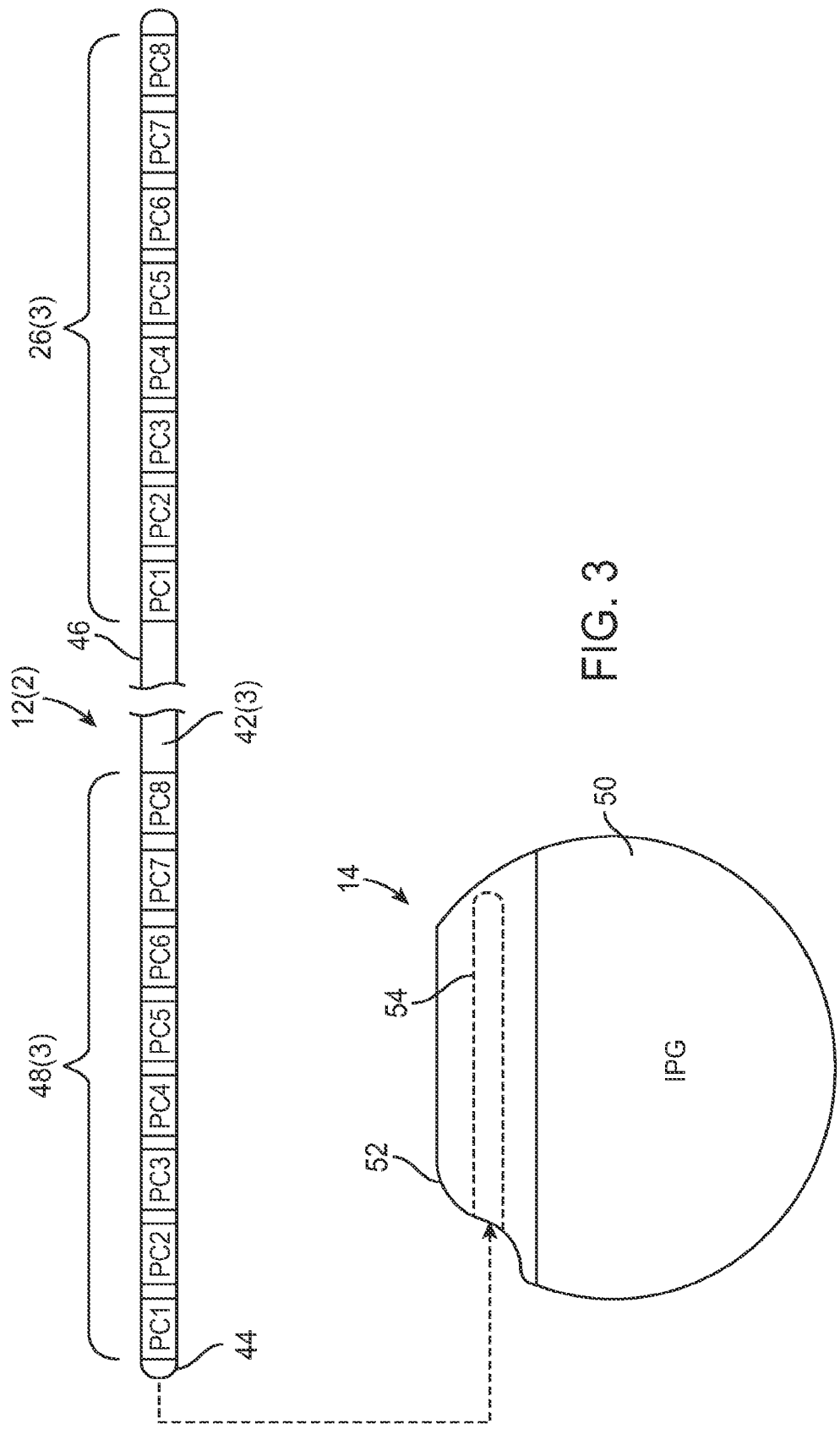
FIG. 3 is a plan view of an implantable pulse generator (IPG) and another embodiment of a percutaneous stimulation lead used in the SCS system of FIG. 1.

Referring to either of FIG. 2 or 3, the IPG 14 comprises an outer case 50 or housing the electronic and other components (described in further detail below). The outer case 50 is composed of an electrically conductive, biocompatible material, such as titanium, and forms a hermetically sealed compartment wherein the internal electronics are protected from the body tissue and fluids. In some cases, the outer case 50 serves as an electrode. The IPG 14 further comprises a connector 52 in which the proximal ends 44 of the lead bodies 42 of the stimulation leads 12 can mate in a manner that electrically couples the electrodes 26 to the electronics contained within the outer case 50. To this end, the connector 52 includes a pair of ports 54 (only one shown in phantom) for receiving the proximal ends 44 of the lead bodies 42(1)/(2) of the surgical paddle lead 12(1) or the proximal end 44 of the lead body 42(3) of the percutaneous lead 12(2) (or proximal ends 44 of the lead bodies 42(3) in the case where two percutaneous leads 12(2) are used). In the case where the lead extensions 24 are used, the ports 54 may instead receive the proximal ends of such lead extensions 24.

As will be described in further detail below, the IPG 14 includes pulse generation circuitry that provides electrical stimulation energy to the electrodes 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), and pulse rate (measured in pulses per second).

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 50, so that the electrical current has a path from the energy source contained within the IPG case 50 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 50 of the IPG 14, so that electrical energy is transmitted between the selected electrode 26 and case 50. Monopolar delivery may also occur when one or more of the lead electrodes 26 are activated along with a large group of lead electrodes located remotely from the one more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 4:
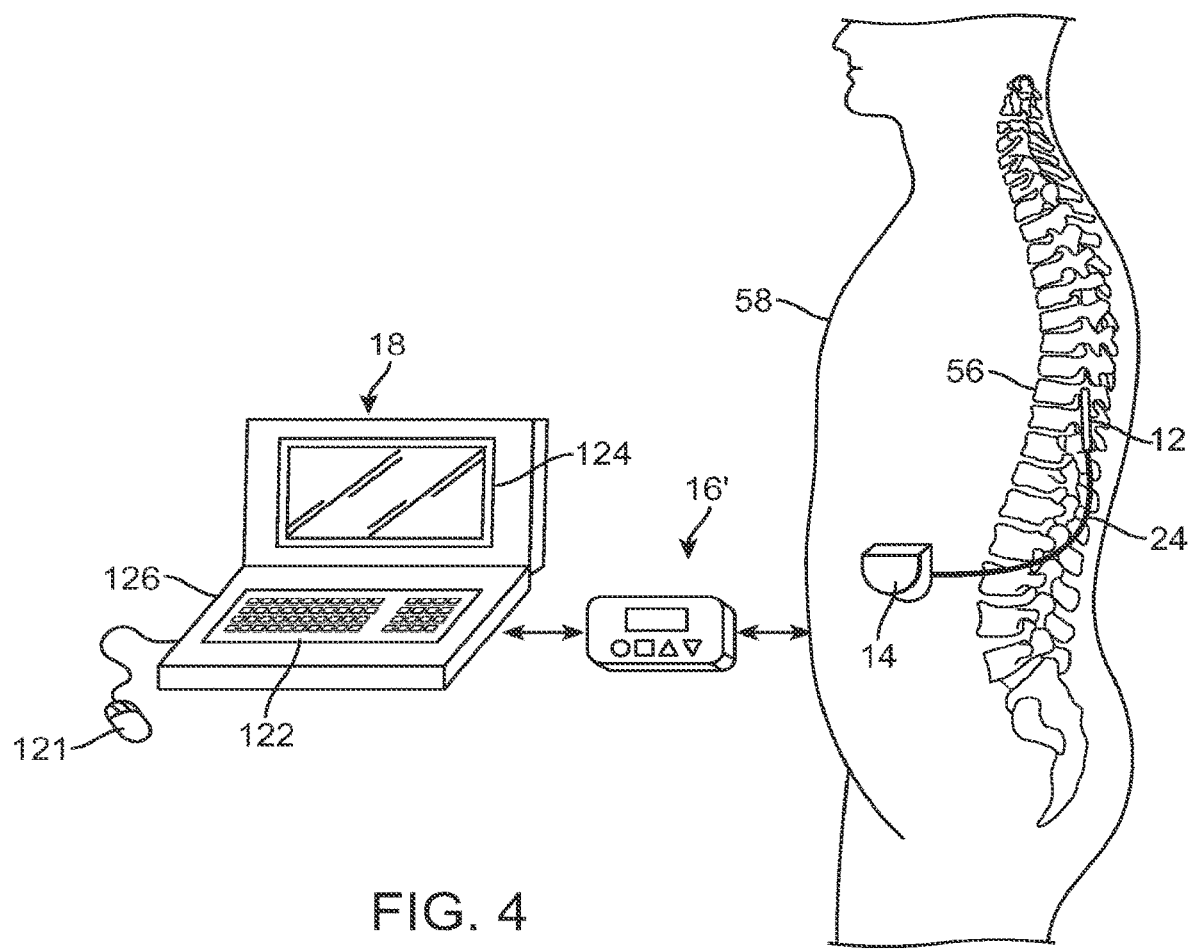
FIG. 4 is a plan view of the SCS system of FIG. 1 in use with a patient.

Referring to FIG. 4, the stimulation lead 12 (either 12(1) or 12(2)) is implanted within the spinal column 56 of a patient 58. The preferred placement of the stimulation lead 12 is adjacent, i.e., resting upon, the spinal cord area to be stimulated. Due to the lack of space near the location where the stimulation lead 12 exits the spinal column 56, the IPG 14 is generally implanted in a surgically-made pocket either in the abdomen or above the buttocks. The IPG 14 may, of course, also be implanted in other locations of the patient's body. The lead extension 24 may be used to facilitate locating the IPG 14 away from the exit point of the stimulation lead 12. After implantation, the IPG 14 is used to provide the therapeutic stimulation under control of the patient.

Figure 5:
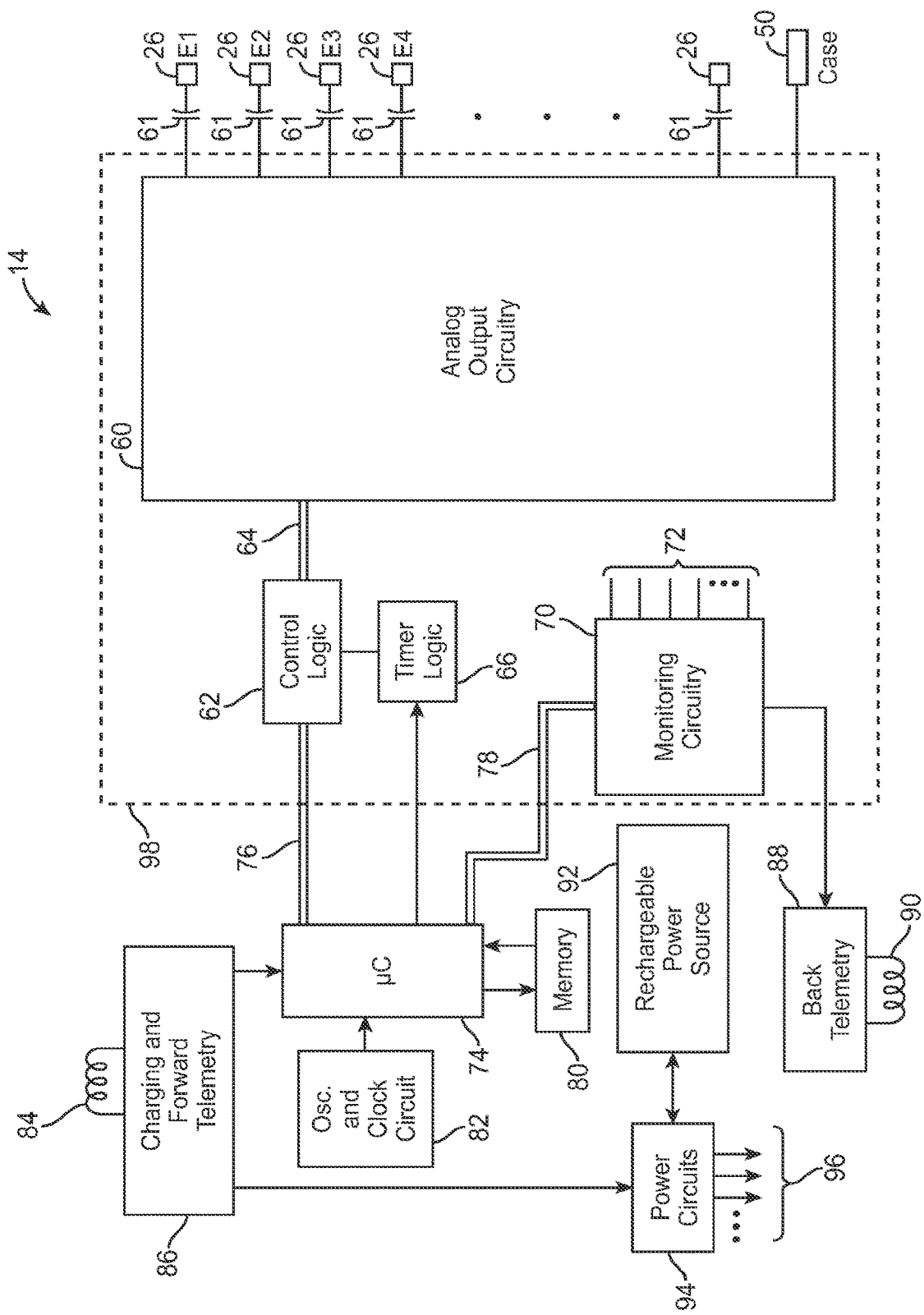
FIG. 5 is a block diagram of the internal components of the IPG of FIG. 1.

Turning next to FIG. 5, the main internal components of the IPG 14 will now be described. The IPG 14 includes analog output circuitry 60 capable of individually generating electrical stimulation pulses via capacitors 61 at the electrodes 26 of specified amplitude under control of control logic 62 over data bus 64. The duration of the electrical stimulation (i.e., the width of the stimulation pulses), is controlled by the timer logic 66. The analog output circuitry 60 may either comprise independently controlled current sources for providing stimulation pulses of a specified and known amperage to or from the electrodes 26, or independently controlled voltage sources for providing stimulation pulses of a specified and known voltage at the electrodes 26. The operation of this analog output circuitry 60, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. Notably, the electrodes 26 fit snugly within the epidural space of the spinal column, and because the tissue is conductive, electrical measurements can be taken between the electrodes 26. Significantly, the monitoring circuitry 70 is configured for taking such electrical measurements, so that, as will be described in further detail below, the CP 18 can automatically identify the specific lead bodies 42 that are connected to the IPG 14. In the illustrated embodiment, the electrical measurements taken by the monitoring circuitry 70 for the purpose of identifying the connected lead bodies, are field potentials. The monitoring circuitry 70 may also measure impedance at each electrode 26 in order to determine the coupling efficiency between the respective electrode 26 and the tissue and/or to facilitate fault detection with respect to the connection between the electrodes 26 and the analog output circuitry 60 of the IPG 14.

Electrical data can be measured using any one of a variety means. For example, the electrical data measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference.

The IPG 14 further comprises processing circuitry in the form of a microcontroller 74 that controls the control logic 62 over data bus 76, and obtains status data from the monitoring circuitry 70 via data bus 78. The IPG 14 additionally, controls the timer logic 66. The IPG 14 further comprises memory 80 and an oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data (including the field potential and impedance data) sensed through the monitoring circuitry 70 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

It should be noted that the diagram of FIG. 5 is functional only, and is not intended to be limiting. Those of skill in the art, given the descriptions presented herein, should be able to readily fashion numerous types of IPG circuits, or equivalent circuits, that carry out the functions indicated and described. It should be noted that rather than an IPG for the neurostimulator, the SCS system 10 may alternatively utilize an implantable receiver-stimulator (not shown) connected to the stimulation lead 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 6:
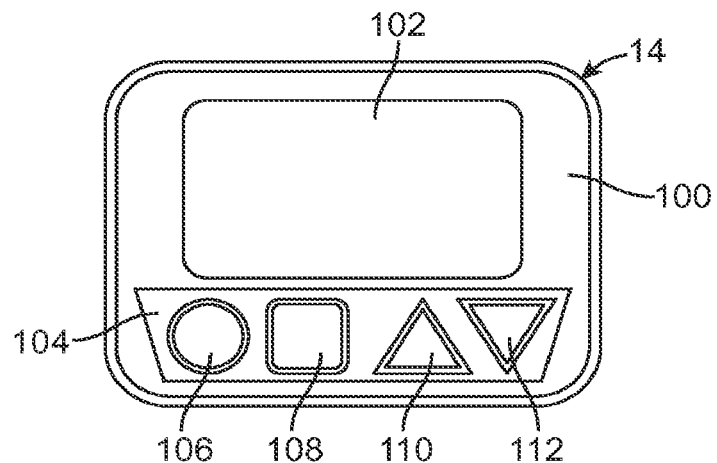
FIG. 6 is a plan view of a remote control that can be used in the SCS system of FIG. 1.

Refuting now to FIG. 6, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touch-screen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can actuated to increment or decrement any of stimulation parameters of the pulse generated by the IPG 14, including pulse amplitude, pulse width, and pulse rate.

Figure 7:
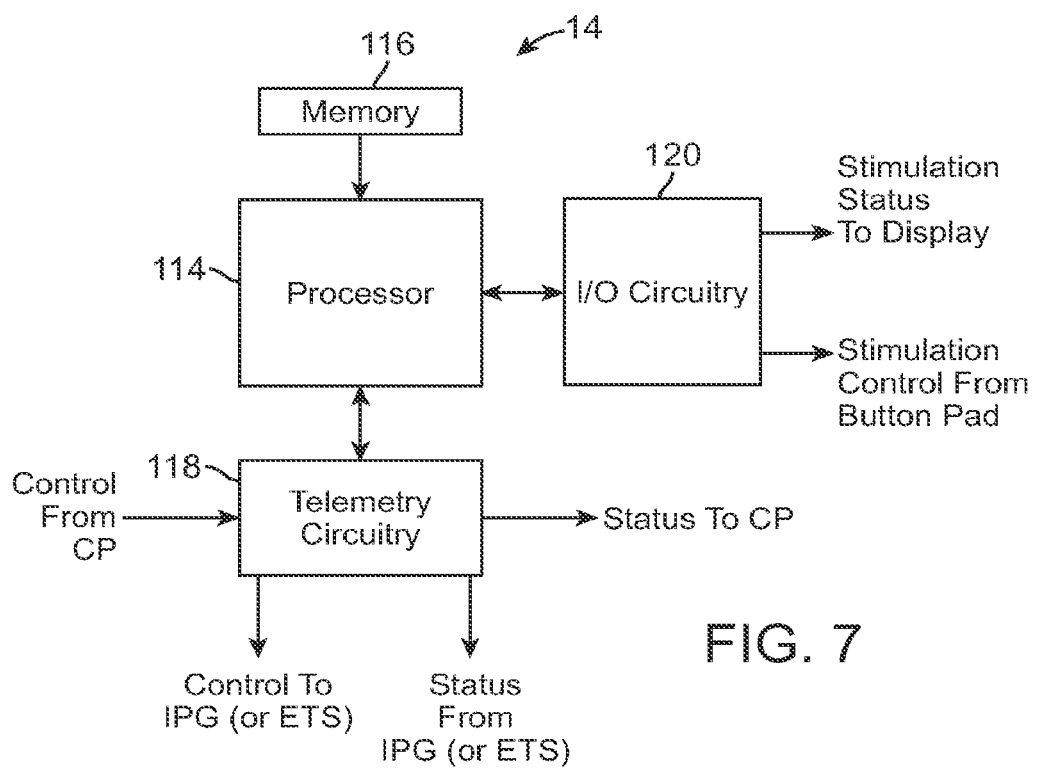
FIG. 7 is a block diagram of the internal componentry of the remote control of FIG. 6.

Referring to FIG. 7, the internal components of an exemplary RC 16 will now be described. The RC 16 generally includes a processor 114 (e.g., a microcontroller), memory 116 that stores an operating program for execution by the processor 114, and telemetry circuitry 118 for transmitting control data (including stimulation parameters and requests to provide status information) to the IPG 14 (or ETS 20) and receiving status information (including the measured electrical data) from the IPG 14 (or ETS 20) via link 34 (or link 32) (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the button pad 104 and transmitting status information to the display screen 102 (shown in FIG. 6). Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 4, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

Figure 8:
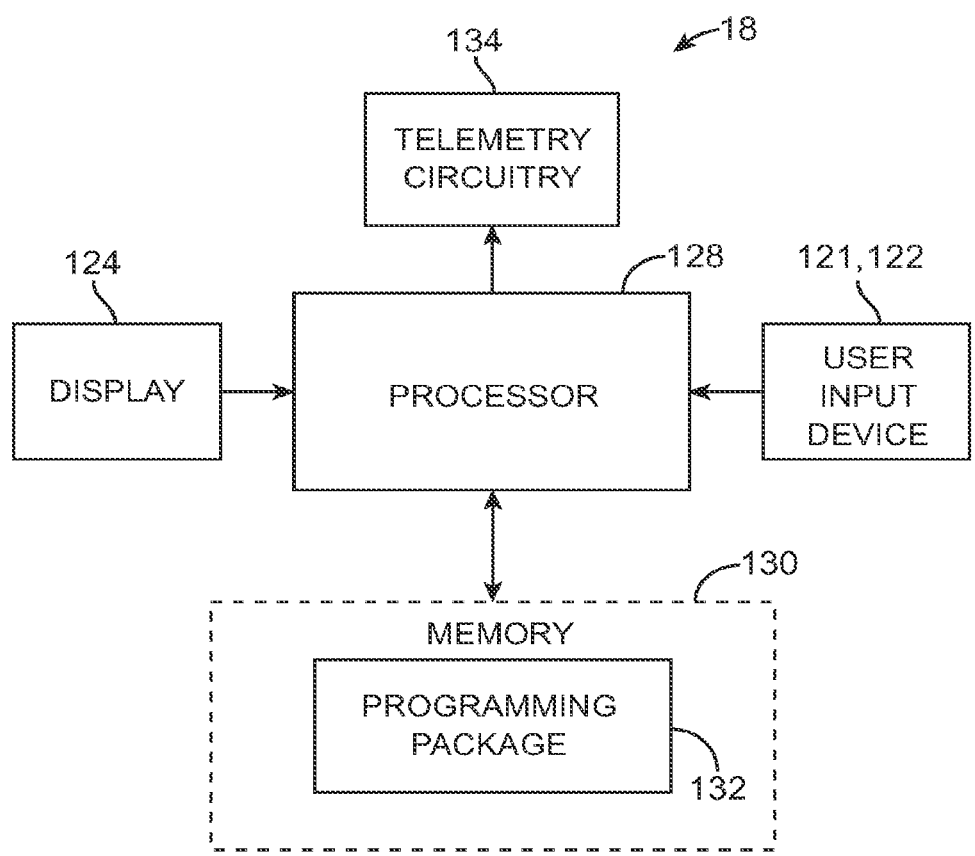
FIG. 8 is a block diagram of the components of a clinician's programmer that can be used in the SCS system of FIG. 1.

To allow the clinician to perform these functions, the CP 18 includes a mouse 121, a keyboard 122, and a programming display screen 124 housed in a case 126. It is to be understood that in addition to, or in lieu of, the mouse 121, other directional programming devices may be used, such as a joystick, or directional keys included as part of the keys associated with the keyboard 122. As shown in FIG. 8, the CP 18 generally includes a processor 128 (e.g., a central processor unit (CPU)) and memory 130 that stores a stimulation programming package 132, which can be executed by the processor 128 to allow a clinician to program the IPG 14 (or ETS 20) and RC 16. The CP 18 further includes telemetry circuitry 134 for downloading stimulation parameters to the RC 16 and uploading stimulation parameters already stored in the memory 116 of the RC 16 via link 36 (shown in FIG. 1). The telemetry circuitry 134 is also configured for transmitting the control data (including stimulation parameters and requests to provide status information) to the IPG 14 (or ETS 20) and receiving status information (including the measured electrical data) from the IPG 14 (or ETS 20) indirectly via the RC 16, Referring further to FIGS. 2 and 3, the CP 18 is configured for automatically identifying the lead body 42 of the stimulation lead 12 that is coupled to the IPG 14 based on an electrical fingerprint created by the lead body 42. In particular, the CP 18 is configured for operating the IPG 14 (i.e., by transmitting a request for status information to the IPG 14 via the RC 16) to measure an electrical fingerprint at the proximal contacts 48 of the lead body 42. Once the lead body 42 is identified, the CP 18 is configured for remapping the outputs of the analog output circuitry 60 (shown in FIG. 5) to the proper electrodes 26 of the stimulation lead 12. Once the lead body 42 is identified and the outputs of the analog output circuitry 60 are mapped to the electrodes 26, the CP 18 can then generate stimulation parameters for use by the IPG 14 based on the identified lead body 42. Thus, the user may insert the lead body 42 into any port 54 of the connector 52 of the IPG 14 without concern that the incorrect connector port is being used.

In the illustrated embodiment, the electrical fingerprint can be correlated to the distances that each electrode 26 is from the other electrodes 26 in the electrode column associated with the distal end of the lead 12.

To this end, the electrical fingerprint is generated and measured by first passing electrical current through each proximal contact 48 associated with the lead body 42 to be identified. The electrical current may be passed in a monopolar arrangement; for example, between the respective proximal contact 48 and the IPG case 50, or in a multipolar arrangement; for example, between the respective proximal contact 48 and one or more other proximal contacts 48 carried by the lead body 42. In response to the passing of electrical current through each respective proximal contact 48, the field potential is measured at each of the other proximal contacts 48 to create field potential profiles for each proximal contact 48.

Thus, each measured field potential is correlated to a distance between the electrode 26 corresponding to the proximal contact 48 through which the electrical current passes and the electrode 26 corresponding to the proximal contact 48 at which the field potential is measured. From this, field potential profiles for each proximal contact 48 can be created, a composite of which can be used to generate a fingerprint for the lead body 42 on which the proximal contacts 48 and corresponding electrodes 26 are carried. Further details regarding field potential measurement techniques are disclosed in U.S. Pat. No. 6,993,384, which is expressly incorporated herein by reference.

The uniqueness of the electrical fingerprints is provided by the different in-line connectivities between the proximal contacts 48 and electrodes 26 associated with the respective lead bodies 42. That is, for the same arrangement of proximal contacts 48, changing the in-line connectivities will change the distances between the electrodes 26 corresponding to the proximal contacts 48, thereby changing the field potential profiles for each proximal contact 48, and the resulting electrical fingerprint for the lead body 42. Notably, without changing the in-line connectivities, the two columns of electrodes 26(1)/(2) associated with the respective lead bodies 42(1)/(2) of the surgical paddle lead 12(1), as well as the electrodes 26(3) associated with the lead body 42(3) of the percutaneous lead 12(2), which may have the same rostro-caudal electrode spacing, will create very similar electrical fingerprints. Thus, the electrical fingerprints created by the lead bodies 42(1)/(2) of the surgical paddle lead 12(1) and by the lead body 42(3) of the percutaneous lead 12(2) would not be distinguishable from each other if the connectivities were the same.

For example, with respect to the percutaneous lead 12(2), the proximal contacts PC1-PC8 may be consecutively connected to the electrodes E1-E8 in a conventional manner. That is, proximal contact is connected to electrode E1, proximal contact PC2 is connected to electrode E2, proximal contact PC3 is connected to electrode E3, proximal contact PC4 is connected to electrode E4, proximal contact PC5 is connected to electrode E5, proximal contact PC6 is connected to electrode E6, proximal contact PC7 is connected to electrode E7, and proximal contact PC8 is connected to electrode E8.

Figure 9:
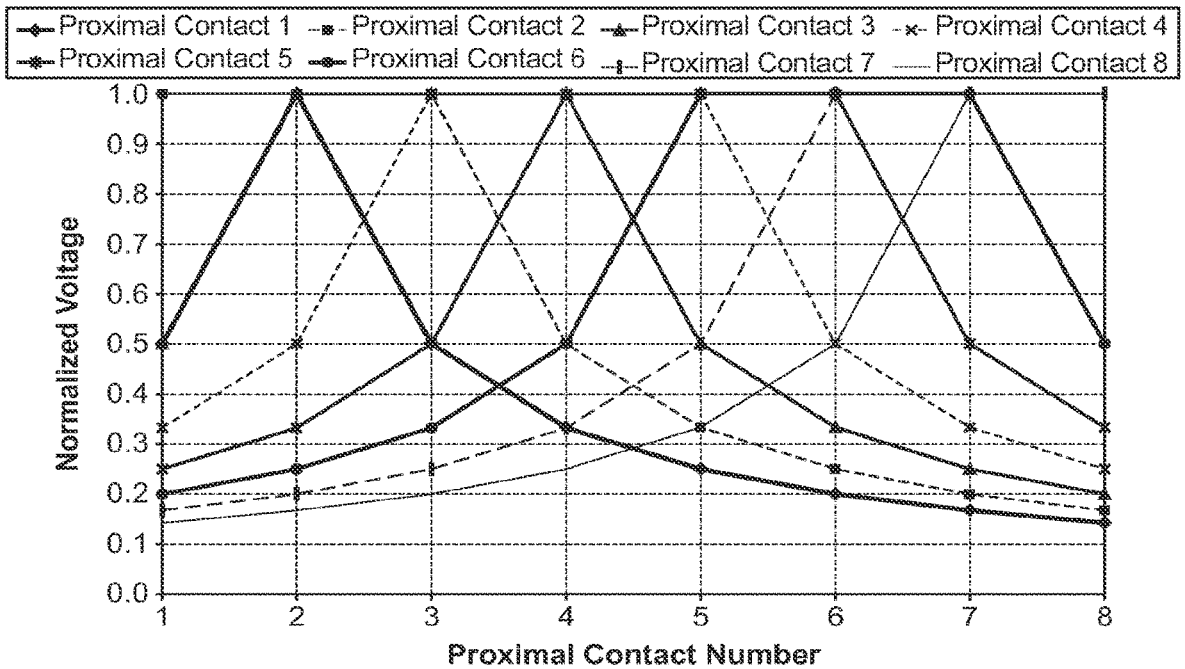
FIG. 9 is a graph of an exemplary electrical fingerprint generated by a lead body of the percutaneous lead of FIG. 3.

As shown in FIG. 9, the resulting electrical fingerprint of the percutaneous lead 12(2) comprises a composite of field potential profiles for respective proximal contacts PC1-PC8. In this case, the field potential profile for each of proximal contacts PC1-PC8 is created by applying electrical current to each respective proximal contact in a monopolar fashion and measuring the field potential at the other proximal contacts. That is, field potentials are measured at proximal contacts PC2-PC8 while electrical current is applied to proximal contact PC1; field potentials are measured at proximal contacts PC1 and PC3-PC8 while electrical current is applied to proximal contact PC2; field potentials are measured at proximal contacts PC1-PC2 and PC4-PC8 while electrical current is applied to proximal contact PC3, etc.

The spacing of the electrodes respectively connected to proximal contacts PC2-PC8 determines the field potential profile of proximal contact PC1. In particular, the field potential profile for proximal contact PC1 has the greatest value at proximal contact PC2, since corresponding electrode E1 is spatially closest to corresponding electrode E2. The field potential profile decreases from this greatest value in the order of proximal contacts PC3-PC8, since the spacing between corresponding electrode E1 and corresponding electrodes E3-E8 incrementally increases in that order.

The spacing of the electrodes respectively connected to proximal contacts PC1 and PC3-PC8 determines the field potential profile of proximal contact PC2. In particular, the field potential profile for proximal contact PC2 has the greatest value at proximal contacts PC1 and PC3, since corresponding electrode E2 is spatially closest to corresponding electrodes E1 and E3. The field potential profile decreases from this greatest value in the order of proximal contacts PC4-PC8, since the spacing between corresponding electrode E2 and corresponding electrodes E4-E8 incrementally increases in that order.

The spacing of the electrodes respectively connected to proximal contacts PC1-PC2 and PC4-PC8 determines the field potential profile of proximal contact PC3. In particular, the field potential profile for proximal contact PC3 has the greatest value at proximal contacts PC2 and PC4, since corresponding electrode E3 is spatially closest to corresponding electrodes E2 and E4. The field potential profile increases to this greatest value from proximal contact PC1, and then decreases from this greatest value in the order of proximal contacts PC5-PC8, since the spacing between corresponding electrode E3 and corresponding electrodes E5-E8 incrementally increases in that order.

The spacing of the electrodes respectively connected to proximal contacts PC1-PC3 and PC5-PC8 determines the field potential profile of proximal contact PC4. In particular, the field potential profile for proximal contact PC4 has the greatest value at proximal contacts PC3 and PC5, since corresponding electrode E4 is spatially closest to corresponding electrodes E3 and E5. The field potential profile increases to this greatest value in the order of proximal contacts PC1-PC2, since the spacing between corresponding electrode E4 and corresponding electrodes E1-E2 incrementally decreases in that order, and then decreases from this greatest value in the order of proximal contacts PC6-PC8, since the spacing between corresponding electrode E4 and corresponding electrodes E6-E8 incrementally increases in that order.

The spacing of the electrodes respectively connected to proximal contacts PC1-PC4 and PC6-PC8 determines the field potential profile of proximal contact PC5. In particular, the field potential profile for proximal contact PC5 has the greatest value at proximal contacts PC4 and PC6, since corresponding electrode E5 is spatially closest to corresponding electrodes E4 and E6. The field potential profile increases to this greatest value in the order of proximal contacts PC1-PC3, since the spacing between corresponding electrode E5 and corresponding electrodes E1-E3 incrementally decreases in that order, and then decreases from this greatest value in the order of proximal contacts PC7-PC8, since the spacing between corresponding electrode E5 and corresponding electrodes E7-E8 incrementally increases in that order.

The spacing of the electrodes respectively connected to proximal contacts PC1-PC5 and PC7-PC8 determines the field potential profile of proximal contact PC6. In particular, the field potential profile for proximal contact PC6 has the greatest value at proximal contacts PC5 and PC7, since corresponding electrode E6 is spatially closest to corresponding electrodes E5 and E7. The field potential profile increases to this greatest value in the order of proximal contacts PC1-PC4, since the spacing between corresponding electrode E6 and corresponding electrodes E1-E4 incrementally decreases in that order, and then decreases from this greatest value to proximal contact PC8.

The spacing of the electrodes respectively connected to proximal contacts PC1-PC6 and PC8 determines the field potential profile of proximal contact PC7. In particular, the field potential profile for the proximal contact PC7 has the greatest value at proximal contacts PC6 and PC8, since corresponding electrode E7 is spatially closest to corresponding electrodes E6 and E8. The field potential profile increases to this greatest value in the order of proximal contacts PC1-PC5, since the spacing between corresponding electrode E7 and corresponding electrodes E1-E5 incrementally decreases in that order.

The spacing of the electrodes respectively connected to proximal contacts PC1-PC7 determines the field potential profile of proximal contact PC8. In particular, the field potential profile for proximal contact PC8 has the greatest value at proximal contact PC7, since corresponding electrode E8 is spatially closest to corresponding electrode E7. The field potential profile increases to this greatest value in the order of proximal contacts PC1-PC6, since the spacing between corresponding electrode E8 and corresponding electrodes E1-E6 incrementally decreases in that order.

With respect to the first lead body 42(1) of the surgical paddle lead 12(1), proximal contacts PC1-PC8 may be connected to electrodes E1-E8 in an unconventional manner. For example, in the illustrated embodiment, proximal contact PC1 is connected to electrode E2, proximal contact PC2 is connected to electrode E5, proximal contact PC3 is connected to electrode E8, proximal contact PC4 is connected to electrode E1, proximal contact PC5 is connected to electrode E4, proximal contact PC6 is connected to electrode E7, proximal contact PC7 is connected to electrode E3, and proximal contact PC8 is connected to electrode E6.

Figure 10:
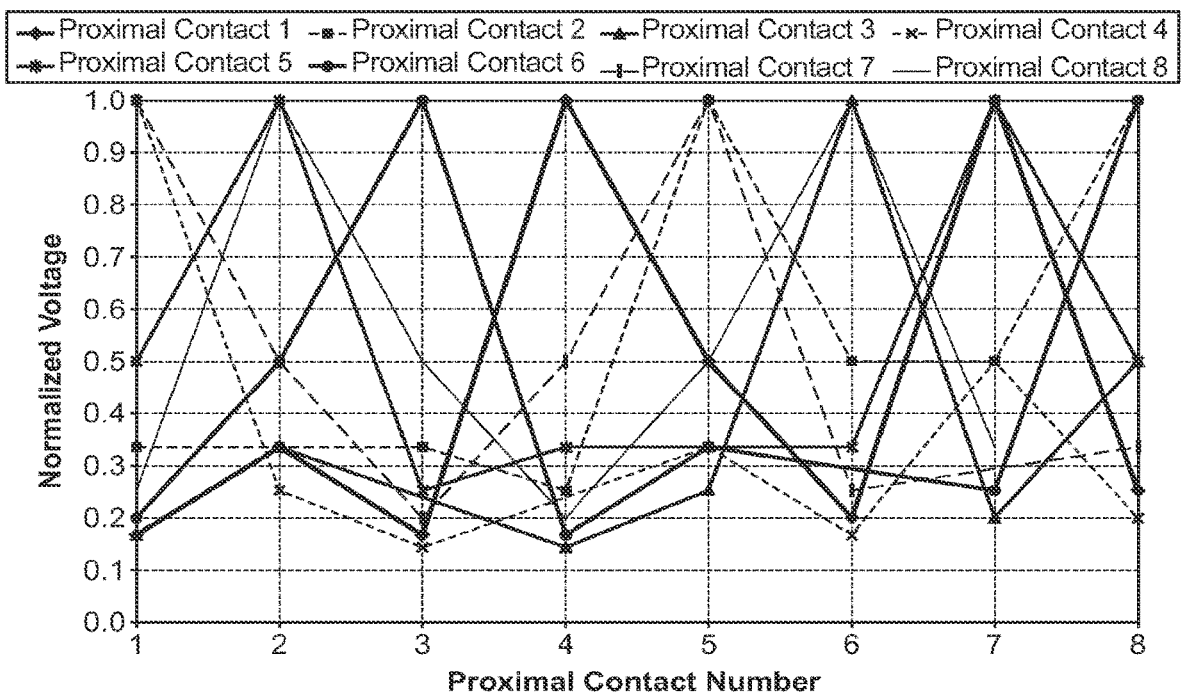
FIG. 10 is a graph of an exemplary electrical fingerprint generated by a first lead body of the surgical paddle lead of FIG. 2.

As shown in FIG. 10, the resulting electrical fingerprint of the first lead body 42(1) of the surgical paddle lead 12(1) comprises a composite of field potential profiles for the respective proximal contacts PC1-PC8. In the same manner described above with respect to the percutaneous lead 12(2), the field potential profile for each of proximal contacts PC1-PC8 is created by applying electrical current to each respective proximal contact in a monopolar fashion and measuring the field potential at the other proximal contacts. In addition, the field potential profile for each proximal contact is determined by the spacing of the electrodes respectively connected to the remaining proximal contacts.

Thus, the field potential profile for proximal contact PC1 has the greatest value at proximal contacts PC4 and PC7, since electrode E2, which is connected to proximal contact PC1, is spatially closest to electrodes E1 and E3, which are respectively connected to proximal contacts PC4 and PC7. The field potential profile for proximal contact PC2 has the greatest value at proximal contacts PC5 and PC8, since electrode E5, which is connected to proximal contact PC2, is spatially closest to electrodes E4 and E6, which are respectively connected to proximal contacts PC5 and PC8. The field potential profile for proximal contact PC3 has the greatest value at proximal contact PC6, since electrode E8, which is connected to proximal contact PC3, is spatially closest to electrode E7, which is connected to proximal contact PC6. The field potential profile for proximal contact PC4 has the greatest value at proximal contact PC1, since electrode E1, which is connected to proximal contact PC4, is spatially closest to electrode E2, which is connected to proximal contact PC1.

The field potential profile for proximal contact PC5 has the greatest value at proximal contacts PC2 and PC7, since electrode E4, which is connected to proximal contact PC5, is spatially closest to electrodes E5 and E3, which are respectively connected to proximal contacts PC2 and PC7. The field potential profile for proximal contact PC6 has the greatest value at proximal contacts PC3 and PC8, since electrode E7, which is connected to proximal contact PC6, is spatially closest to electrodes E8 and E7, which are respectively connected to proximal contacts PC3 and PC8. The field potential profile for proximal contact PC7 has the greatest value at proximal contacts PC1 and PC5, since electrode E3, which is connected to proximal contact PC7, is spatially closest to electrodes E2 and E4, which are respectively connected to proximal contacts PC1 and PC5. The field potential profile for proximal contact PC8 has the greatest value at proximal contacts PC2 and PC6, since electrode E6, which is connected to proximal contact PC8, is spatially closest to electrodes E5 and E7, which are respectively connected to proximal contacts PC2 and PC6.

Unlike with the percutaneous lead 12(2) where the field potential profiles for each of the proximal contacts PC1-PC5 incrementally increases and decreases from the greatest values, as can be seen in FIG. 10, the field potential profile for each of proximal contacts PC1-PC8 varies erratically from the greatest values, because proximal contacts PC1-PC8 are not consecutively connected to electrodes E1-E8 with respect to the first lead body 42(1) of the surgical paddle lead 12(1).

With respect to the second lead body 42(2) of the surgical paddle lead 12(1), the proximal contacts PC1-PC8 may be connected to electrodes E1-E8 in another unconventional manner. For example, in the illustrated embodiment, proximal contact PC1 is connected to electrode E7, proximal contact PC2 is connected to electrode E6, proximal contact PC3 is connected to electrode E8, proximal contact PC4 is connected to electrode E2, proximal contact PC5 is connected to electrode E4, proximal contact PC6 is connected to electrode E5, proximal contact PC7 is connected to electrode E3, and proximal contact PC8 is connected to electrode E1.

Figure 11:
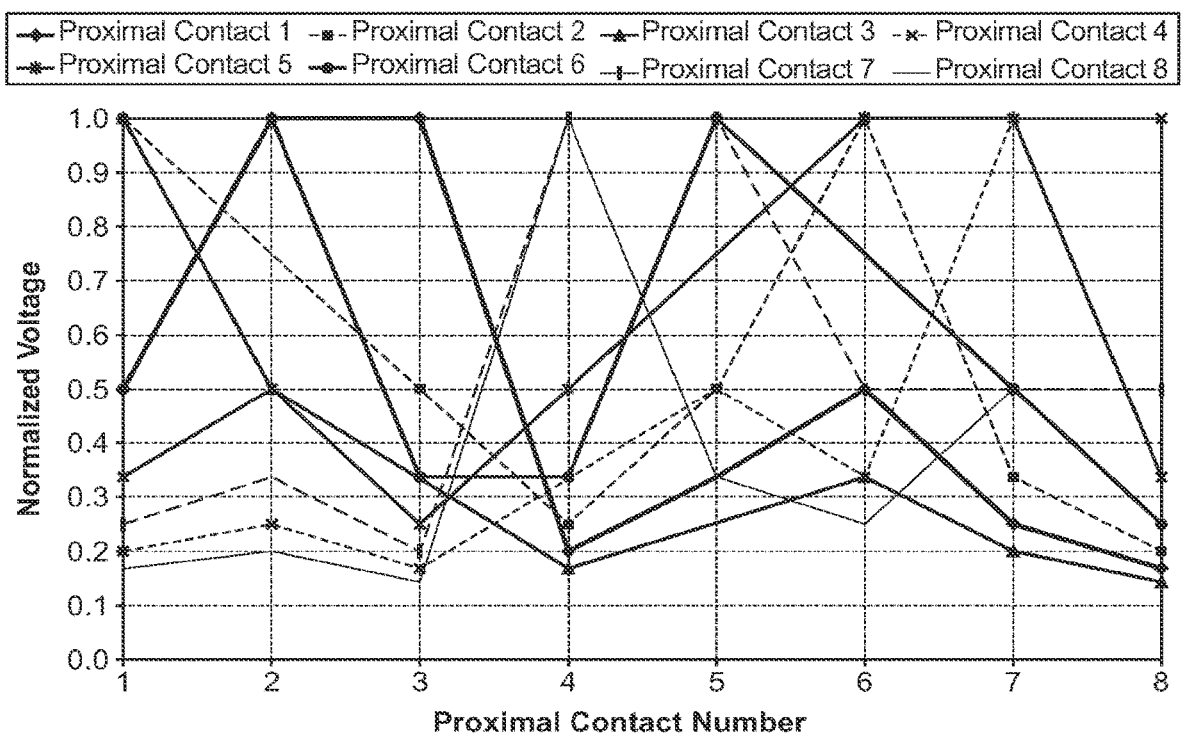
FIG. 11 is a graph of an exemplary electrical fingerprint generated by a second lead body of the surgical paddle lead of FIG. 2.

As shown in FIG. 11, the resulting electrical fingerprint, of the second lead body 42(2) of the surgical paddle lead 12(l) comprises a composite of field potential profiles for the respective proximal contacts PC1-PC8. In the same manner described above with respect to the percutaneous lead 12(2), the field potential profile for each of proximal contacts PC1-PC8 is created by applying electrical current to each respective proximal contact in a monopolar fashion and measuring the field potential at the other proximal contacts. In addition, the field potential profile for each proximal contact is determined by the spacing of the electrodes respectively connected to the remaining proximal contacts.

Thus, the field potential profile for proximal contact PC1 has the greatest value at proximal contacts PC2 and PC3, since electrode E7, which is connected to proximal contact PC1, is spatially closest to electrodes E6 and E8, which are respectively connected to proximal contacts PC2 and PC3. The field potential profile for proximal contact PC2 has the greatest value at proximal contacts PC1 and PC6, since electrode E6, which is connected to proximal contact PC2, is spatially closest to electrodes E7 and E5, which are respectively connected to proximal contacts PC1 and PC6. The field potential profile for proximal contact PC3 has the greatest value at proximal contact PC1, since electrode E8, which is connected to proximal contact PC3, is spatially closest to electrode E7, which is connected to proximal contact PC1. The field potential profile for proximal contact PC4 has the greatest value at proximal contacts PC7 and PC8, since electrode E2, which is connected to proximal contact PC4, is spatially closest to electrodes E3 and E1, which are respectively connected to proximal contacts PC7 and PC8.

The field potential profile for proximal contact PC5 has the greatest value at proximal contacts PC6 and PC7, since electrode E4, which is connected to proximal contact PC5, is spatially closest to electrodes E5 and E3, which are respectively connected to proximal contacts PC6 and PC7. The field potential profile for proximal contact PC6 has the greatest value at proximal contacts PC2 and PC5, since electrode E5, which is connected to proximal contact PC6, is spatially closest to electrodes E6 and E5, which are respectively connected to proximal contacts PC2 and PC5. The field potential profile for proximal contact PC7 has the greatest value at proximal contacts PC4 and PC5, since electrode E3, which is connected to proximal contact PC7, is spatially closest to electrodes E2 and E4, which are respectively connected to proximal contacts PC4 and PC5. The field potential profile for proximal contact PC8 has the greatest value at proximal contact PC4, since electrode E1, which is connected to proximal contact PC8, is spatially closest to electrode E2, which is connected to proximal contact PC4.

Again, because proximal contacts PC1-PC8 are not consecutively connected to electrodes E1-E8 with respect to the second lead body 42(2) of the surgical paddle lead 12(1), the field potential profile for each of proximal contacts PC1-PC8 varies erratically from the greatest values, as can be seen in FIG. 11.

The CP 18 automatically identifies the specific lead body 42 connected to the IPG 14 (or ETS 20) based on the electrical fingerprints measured by the IPG 14 (or ETS 20). To this end, the memory 130 stores a plurality of reference electrical fingerprints corresponding to the different lead bodies 42. The reference electrical fingerprints can be generated from expected electrical fingerprints computed from point sources of the electrodes. Alternatively, the reference electrical fingerprints can be generated from actual measurements taken from the proximal contacts of leads. In any event, the processor 128 is configured for comparing the electrical fingerprint measured by the IPG 14 to each of the reference electrical fingerprints stored in memory 130, determining a match between the measured electrical fingerprint and one of the reference electrical fingerprints, and identifying the lead body 42 connected to the IPG 14 as the lead body corresponding to the matching one of the reference electrical fingerprints.

In the illustrated embodiment, the processor 128 is configured for computationally comparing data points in the measured electrical fingerprint to data points in each of the reference electrical fingerprints, and determining a match between the measured electrical fingerprint and the reference electrical fingerprint based on the comparison function.

For example, one comparison function that can be used is a correlation coefficient function, such as a Pearson Correlation Coefficient function, which can be expressed as the following equation:

$$r = \frac{\sum_i (MEAS_i - M_{MEAS})(REFi - M_{REF})}{sqrt\left(\sum_i (MEAS_i - M_{MEAS}) \sum_i (REFi - M_{REF})^2\right)},$$

where r is the coefficient, MEAS represents the data set of the electrical fingerprint measured by the IPG 14, REF represents the data set of the reference electrical fingerprint to which the data of the measured electrical fingerprint is currently be compared, M represents the mean of the data set (either measured or reference), and i represents a single element of the data set (either measured or reference).

Advantageously, the correlation coefficient is not sensitive to magnitude scaling, and ranges from −1 (perfect inverse correlation) to 1 (perfect correlation). Thus, the correlation coefficient would be close to 1 for a match between the measured electrical fingerprint and the reference electrical fingerprint and less than a threshold value (e.g., 0.9) for a mismatch between the measured electrical fingerprint and the reference electrical fingerprint.

The expected correlation coefficient generated by performing a Pearson Correlation Coefficient function on the electrical fingerprints illustrated in FIGS. 9 and 10 is −0.35; the expected correlation coefficient generated by performing a Pearson Correlation Coefficient function on the electrical fingerprints illustrated in FIGS. 9 and 11 is 0.25; and the expected correlation coefficient generated by performing a Pearson Correlation Coefficient function on the electrical fingerprints illustrated in FIGS. 10 and 11 is 0.14. Thus, the auto-identification feature of the processor 128 is robust against mismatching a connected lead body 42 to an identified lead body.

Another comparison function that can b used is a least squares based function, and in particular, a sum of squared differences function, which can be expressed as the following equation:

$$SSD = \sum_i \left((MEAS_i - REF_i)^2\right),$$

where SSD is the sum of squared difference, and MEAS, REF, and i have been defined above. The SSD function measures the difference between the data set of the measured electrical fingerprint and the data set of the reference electrical fingerprint. With this function, the reference electrical fingerprint that results in the minimum sum of squared difference is the one whose corresponding lead body is selected as the identified lead body.

Other comparison functions, including cross-correlation functions, wavelet functions, and associated matching measures, may be alternatively used.

It should be noted that the data sets of the electrical fingerprints may be derived from a subset of the electrodes before initially performing the computation function. For example, the auto-identification feature should be robust against open contacts and high impedances. In this case, a smaller number (perhaps one or two) of the proximal contacts 48 exhibiting high impedance values can be ignored. This increased robustness would come at the expense of a reduced number of unique electrical fingerprints that could be encoded into proximal ends of lead bodies.

Notably, a properly seated connection between the proximal contacts 48 of a respective lead body 42 and the connector 52 of the IPG 14 is important for the auto-identify feature to operate properly, since any shift in connector alignment will result in an electrical fingerprint mismatch even if the measured electrical fingerprint is compared to an otherwise matching reference electrical fingerprint. In particular, electrical fingerprints that correspond to various misalignment conditions (conditions where the proximal contacts are misaligned with the connector of the IPG) can be generated. In this case, high impedance measurements, which indicate a misalignment condition, will be retained as part of the electrical fingerprint. The measured electrical fingerprint can then be compared to these reference misalignment electrical fingerprints, so that the CP 18 can automatically identify and correct the misalignment condition.

Also, repeated electrical fingerprint measurements made over time increase the probability of eventually obtaining an incorrect lead body identification. To avoid this, the processor 128 is configured for storing the lead body identifier within the memory 130 when it has first been made and for updating the lead body identifier only when the stimulation lead is replaced and the auto-identify feature is again performed. The auto-identify feature can be performed whenever a programming session is started, but a new lead body identification, if found to be different from the saved lead body identification, would require user confirmation to be applied and overwritten into the memory 130. This confirmation may also be needed the first time that the lead bodies are connected to the IPG 14 if found to be different from the default consecutive in-line connectivity.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for delivering electrical stimulation to a patient using a stimulator connected to a neurostimulation lead including one or more lead bodies and distal electrodes, the one or more lead bodies each including proximal contacts electrically connected to the respective distal electrodes, the method comprising:

creating a set of field potential profiles for each lead body of the one or more lead bodies, including:
    passing an electrical current through each contact of the proximal contacts of the each lead body;
    measuring field potentials each at a contact of the proximal contacts, the field potentials resulting from the passing of the electrical current through the each contact; and
    creating the field potential profile for the each contact using the measured field potentials;
comparing the created set of field potential profiles of the each lead body to each of stored one or more sets of reference field potential profiles, the stored one or more sets each predetermined for a lead body of the one or more lead bodies; and
determining information related to programming of the stimulator using an outcome of the comparison.

2. The method of claim 1, further comprising updating the stored set of reference field potential profiles of the each lead body in response to the created set of field potential profiles of the each lead body being different from the stored set of reference field potential profiles of the each lead body.

3. The method of claim 1, further comprising storing the created set of field potential profiles of the each lead body as an additional set of reference field potential profiles of the each lead body in response to the created set of field potential profiles of the each lead body being different from the stored set of reference field potential profiles of the each lead body.

4. The method of claim 1, further comprising automatically identifying a misalignment between the stimulator and the neurostimulation lead using the outcome of the comparison.

5. The method of claim 1, further comprising automatically identifying a lead body of the one or more lead bodies using the outcome of the comparison.

6. The method of claim 5, further comprising automatically identifying the lead body during each programming session of the stimulator.

7. The method of claim 1, wherein comparing the created set of field potential profiles of the each lead body to the stored one or more sets of reference field potential profiles comprises performing a comparison function computationally comparing data points in each profile of the created set of field potential profiles of the each lead body to data points in each respective profile of each set of reference field profiles of the stored one or more sets of reference field potential profiles.

8. The method of claim 7, wherein performing the comparison function comprises generating correlation coefficients for a relationship between the created set of field potential profiles of the each lead body and the stored set of reference field potential profiles of each set of reference field profiles of the stored one or more sets of reference field potential profiles.

9. The method of claim 1, further comprising programming the stimulator for delivering spinal cord stimulation using the outcome of the comparison.

10. The method of claim 9, wherein creating the set of field potential profiles for the each lead body comprises creating a set of field potential profiles for each lead body of multiple lead bodies of a surgical paddle lead configured for delivering the spinal cord stimulation.

11. A system for delivering electrical stimulation to a patient using a stimulator connected to a neurostimulation lead including one or more lead bodies and distal electrodes, the one or more lead bodies each including proximal contacts electrically connected to the respective distal electrodes, the system comprising:
    a programmer configured to program the stimulator, the programmer configured to:
        create a set of field potential profiles for each lead body of the one or more lead bodies by programming the stimulator to deliver an electrical current through each contact of the proximal contacts of the each lead body and to measure field potentials each at a contact of the proximal contacts, the field potentials resulting from the delivery of the electrical current through the each contact, and creating the field potential profile for the each contact using the measured field potentials;
        compare the created set of field potential profiles of the each lead body to each of one or more sets of reference field potential profiles stored in the programmer, the stored one or more sets each predetermined for a lead body of the one or more lead bodies; and
        determine information related to programming of the stimulator using an outcome of the comparison.

12. The system of claim 11, wherein the programmer is further configured to automatically identify a misalignment between the stimulator and the neurostimulation lead using the outcome of the comparison.

13. The system of claim 11, wherein the programmer is further configured to automatically identify a lead body of the one or more lead bodies using the outcome of the comparison.

14. The system of claim 11, wherein the programmer is configured to computationally compare data points in each profile of the created field potential profiles of the each lead body to data points in each respective profile of the reference field potential profiles of the each lead body.

15. The system of claim 14, wherein the programmer is configured to generate correlation coefficients for a relationship between the created field potential profiles of the each lead body and the reference field potential profiles of the each lead body.

16. The system of claim 11, comprising an implantable pulse generator configured to be the stimulator, and wherein the programmer is configured to program the implantable pulse generator to apply a spinal cord stimulation therapy to the patient.

17. A non-transitory computer-readable storage medium including instructions, which when executed by a system, cause the system to perform a method for delivering electrical stimulation to a patient using a stimulator connected to a neurostimulation lead including one or more lead bodies and distal electrodes, the one or more lead bodies each including proximal contacts electrically connected to the respective distal electrodes, the method comprising:
    creating field potential profiles for each lead body of the one or more lead bodies, including:
        passing an electrical current through each contact of the proximal contacts of the each lead body;
        measuring field potentials each at a contact of the proximal contacts, the field potentials resulting from the passing of the electrical current through the each contact; and
        creating the field potential profile for the each contact using the measured field potentials;
    comparing the created set of field potential profiles of the each lead body to each of stored one or more sets of reference field potential profiles, the stored one or more sets each predetermined for a lead body of the one or more lead bodies; and determining information related to programming of the stimulator using an outcome of the comparison.

18. The non-transitory computer-readable storage medium of claim 17, wherein the method further comprises identifying a misalignment between the stimulator and the neurostimulation lead using the outcome of the comparison.

19. The non-transitory computer-readable storage medium of claim 17, wherein the method further comprises automatically identifying a lead body of the one or more lead bodies using the outcome of the comparison.

20. The non-transitory computer-readable storage medium of claim 17, wherein comparing the created set of field potential profiles of the each lead body to each of the stored one or more sets of reference field potential profiles comprises performing a comparison function that computationally compares data points in each profile of the created set of field potential profiles of the each lead body to data points in each respective profile of the each of the stored one or more sets of reference field potential profiles.

* * * * *